United States Patent [19]

Lowd et al.

[11] Patent Number: 4,531,245
[45] Date of Patent: Jul. 30, 1985

[54] PERSONAL URINAL DEVICE

[76] Inventors: David L. Lowd, 13 Clifton Ave.; Gerald J. Sobolewski, 85 Wheeler Ave.; Lynne R. Lowd, 13 Clifton Ave.; Barbara Sobolewski, 85 Wheeler Ave., all of Salem, N.H. 03079

[21] Appl. No.: 587,205

[22] Filed: Mar. 7, 1984

[51] Int. Cl.³ .............................................. A47K 11/00
[52] U.S. Cl. .................................. 4/144.3; 141/337; 604/347; 604/349
[58] Field of Search ................... 4/144.1, 144.2, 144.3, 4/144.4, 307, 310, 311, 450–454, 453, 449; 604/329, 347, 349, 317, 356; 141/337

[56] References Cited

U.S. PATENT DOCUMENTS

| | | | |
|---|---|---|---|
| 1,396,382 | 11/1921 | Pieters | 4/450 |
| 1,660,442 | 2/1928 | Hampton | 141/337 |
| 1,928,170 | 9/1933 | Dwork | 4/144.4 |
| 2,066,400 | 1/1937 | Hale | 4/144.3 |
| 2,182,254 | 12/1939 | Farrell | 4/144.3 |
| 2,358,850 | 9/1944 | Chenault | 4/144.1 |
| 3,131,403 | 5/1964 | Hill | 4/144.3 |
| 3,432,864 | 3/1969 | Schwartz | 4/144.2 |
| 3,432,865 | 3/1969 | Schwartz | 4/144.2 |
| 3,575,225 | 4/1971 | Muheim | 604/356 |
| 3,600,719 | 8/1971 | Karr | 4/144.2 |
| 3,927,426 | 12/1975 | Geddes | 4/144.3 |
| 3,995,329 | 12/1976 | Williams | 4/144.3 |
| 4,058,995 | 11/1977 | Greaves | 141/337 |

FOREIGN PATENT DOCUMENTS 679726 7/1939 Fed. Rep. of Germany ...... 604/317

*Primary Examiner*—Stephen Marcus
*Assistant Examiner*—Linda J. Sholl
*Attorney, Agent, or Firm*—Edward A. Gordon

[57] ABSTRACT

A urinary device which is principally but not exclusively intended for female and which enables urination from a standing or sitting position. The urinal device which provides for both conduction and collection modes comprises an upper bowl member and a removable lower conducting and/or collector member which is suspended from the lower portion of the bowl member. The lower conducting and collector member is formed of a waterproof material which is sufficiently relatively flexible whereby it can be folded or compressed upon itself and stored within the bowl member until use when it is extended to operating position. The distal end of the lower conducting/collector member is provided with a tapered discharge opening and with means for sealing the discharge opening to contain the discharged urine when used in the collecting mode. The upper opening of the bowl member is contoured to envelope the perineum when in position for use. The upper bowl cover when in the closed position provides a liquid tight seal and when in the open position extends forwardly and serves as a handle which aids in holding and manipulating the urinal device into and out of position for use. In a preferred embodiment the bowl member is provided with a lower cover to maintain the lower conductor/collector member in folded position within the bowl member. In the folded and cover closed mode, the urinal device can be carried in a woman's handbag and is contoured to be esthetically pleasing.

6 Claims, 11 Drawing Figures

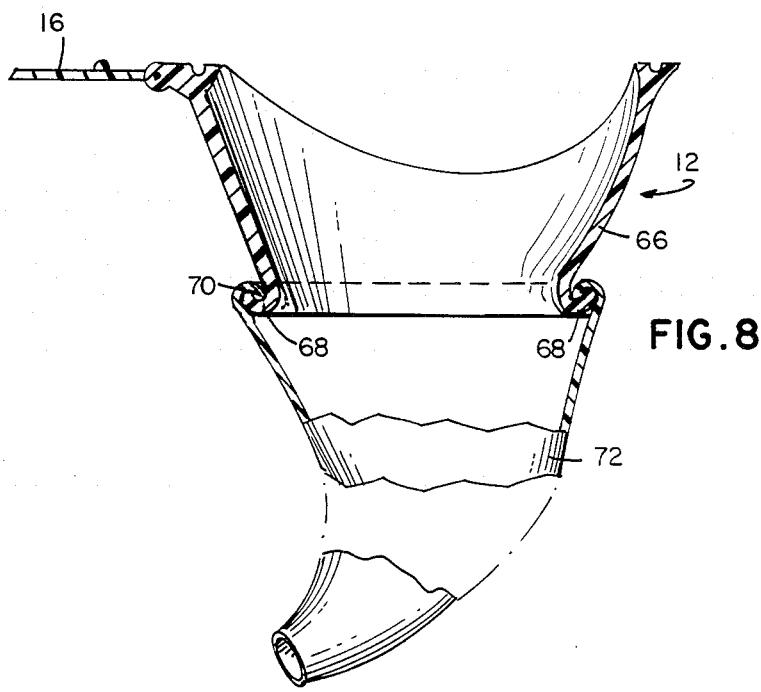
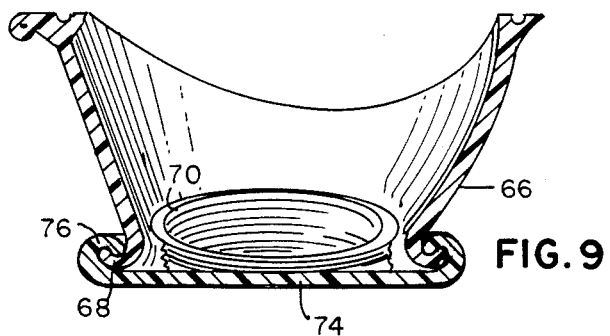

PERSONAL URINAL DEVICE

BACKGROUND OF THE INVENTION

1. Field of the Invention

This invention relates generally to urinary devices and more particularly to an improved personal urinary device which is principally but not exclusively intended for a female and which enables urination from a standing or sitting position.

2. Description of the Prior Art

Various devices have been proposed but these are primarily for use by bed confined female patients in hospitals or the like, or provide only for urine conduction. Heretofore such urinal devices are exemplified by U.S. Pat. Nos. 3,131,430, 4,309,779, 3,964,111 and 4,023,216.

SUMMARY OF THE INVENTION

The device of the present invention comprises an upper bowl member and a removable lower conducting and collector member which is suspended from the lower portion of the bowl member. The lower conducting and collector member is formed of a water proof material which is sufficiently relatively flexible so that it is folded or compressed upon itself and stored within the bowl member where it remains until use when it is extended to operating position. The distal end of the lower conducting/collector member is provided with a discharge opening and with means for sealing the discharge opening to contain the discharged urine when used in the collector mode.

The upper edge of the bowl member is provided with a generally elliptical, contoured opening to duplicate that region of the perineum extending from the vaginal opening anteriorly and laterally generally concident with the labia majora, to a point anterior of the urethra to provide a fluid tight seal therewith in such region. The bowl member is provided with a top cover which is contoured on the lower edge to correspond with the bowl member in the closed position and provide a liquid tight seal.

The upper bowl cover when in the open position extends forwardly and serves as a handle which permits it to be gripped by the thumb and fingers of one hand of the user, aids in manipulating the urinal device into and out of position and to be held firmly in position for use. In a preferred embodiment the bowl member is provided with a lower bowl cover to maintain the lower conductor/collector member in folded position within the bowl member. In the folded and cover closed mode, the urinal device can be carried in a woman's handbag. The outer configuration of the urinal device is preferably contoured to be esthetically pleasing.

When in the open operating position, the device enables a woman to urinate from a standing position and during urination, to direct the stream issuing from the device to a suitable spot. With the discharge opening sealed, the urinary device can be used by a man or woman in a standing or sitting position as a temporary storage container for the discharged urine.

In alternative embodiments of the invention, the lower conducting/collector member or the entire device can be of reusable or disposable construction and when in the reusable form is constructed of a material which is washable for reuse by the user.

DESIRED OBJECTS AND ADVANTAGES OF THE INVENTION

It is a desired object of the present invention to provide a personal urinal device that is easily portable and that enables a female to urinate whether in a standing or seated position.

It is still another desirable object of the invention to provide a urinary device that enables females to urinate without assuming unstable or dangerous positions where footing may be unsecure (hilly or mountainous terrain, etc.).

Another desirable object of the invention is to provide a urinary device which enables females during urination, to direct the stream, issuing from the device to a suitable spot.

A still further desirable object of the invention is to provide a personal urinary device which may be used by male or females in the standing or sitting position and serves as a temporary urine receptable or collector where other facilities are not readily available.

Another object of the present invention is to provide a urinary device which, where sanitary facilities are poor, enables a female to avoid contact with dirty toilet seats and their associated hazards.

Another desired object of the invention is to provide a personal urinal device that enables a female to avoid painful abstention caused by inadequate sanitary facilities.

A still further desirable object of the invention is to provide an improved perineum - covering urinal device which has permanent and disposable elements made of foldable or compressable and liquid proof material such as a suitable plastic or waterproof paper.

A still further desirable object of the present invention is to provide a personal urinal device which may be manipulated into and out of position as well as held firmly in position by the thumb and fingers of one hand of the user.

The invention accordingly comprises the apparatus possessing the construction, combination of elements and arrangement of parts which are exemplified in this disclosure and the scope of the application of which will be indicated in the claims.

DESCRIPTION OF THE DRAWINGS

For a fuller understanding of the nature and desired objects of the invention, reference should be had to the following detailed description taken in connection with the accompanying drawings wherein like reference characters denote corresponding parts throughout the several views and wherein:

FIG. 8 is a fragmentary perspective view of an alternate embodiment of the urinal device of the present invention;

FIG. 9 is a fragmentary sectional view of the lower portion of the device of FIG. 8 in the closed position with the lower conductor member stored within;

FIG. 1 is a view in perspective showing the use of the personal urinal device embodying the invention by a female in the sitting position.

DESCRIPTION OF THE PREFERRED EMBODIMENTS

Figure 1:
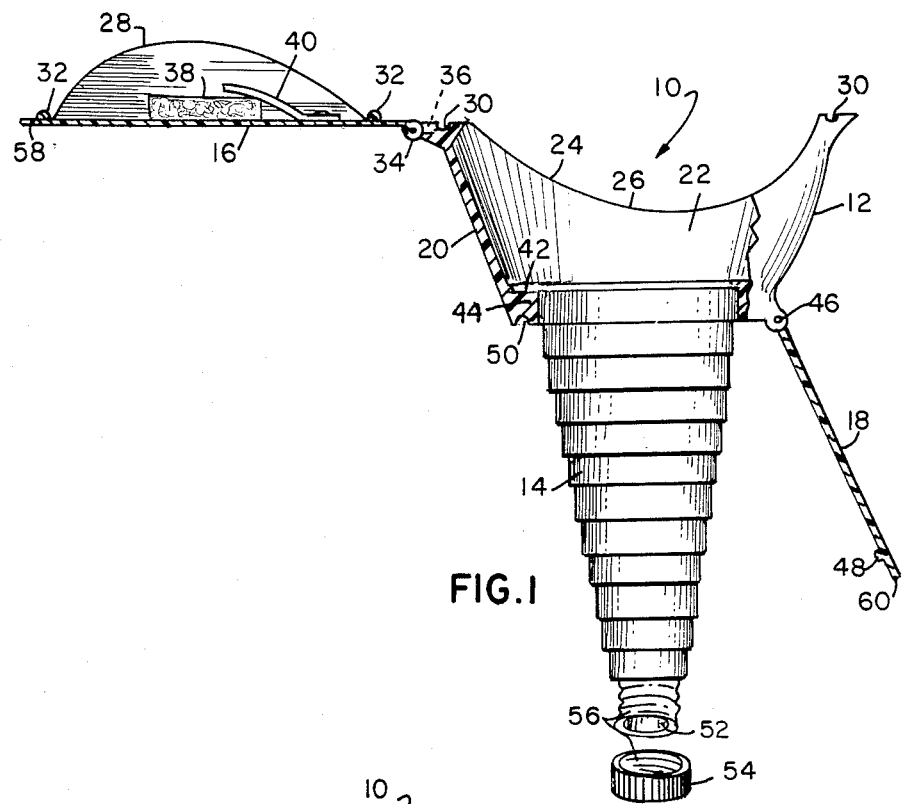
FIG. 1 is a fragmentary partially sectional perspective view of the urinal device of the present invention.
Figure 2:
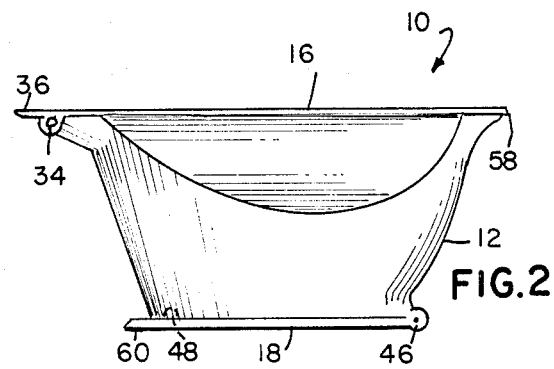
FIG. 2 is a perspective view of the urinal device of FIG. 1 shown in closed position.

Referring now more particularly to FIGS. 1 through 5 of the drawings there is shown an urinal device embodying the invention indicated generally at 10. The urinal device 10 comprises an upper bowl member 12 a lower conductor/collector member 14. The bowl member 12 is provided with an upper closure or cover member 16 and a lower closure or cover member 18.

Figure 3:
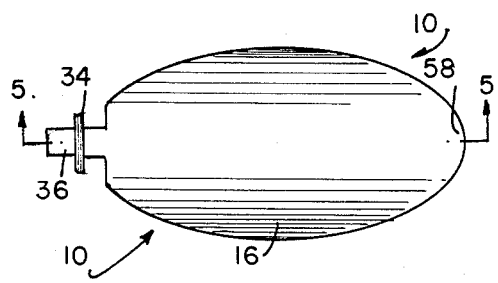
FIG. 3 is a top perspective view of the urinal device of FIG. 2.
Figure 4:
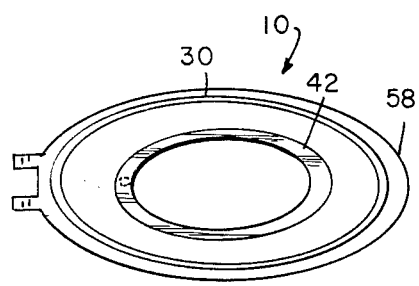
FIG. 4 is a bottom perspective view of the urinal device of FIG. 2.

The housing 20 of bowl 12 tapers downwardly and has a generally overall oval configuration as best seen in FIGS. 3 and 4. The top opening 22 is formed by the upper edge 24 of bowl 12. The edge 24 slopes upwardly to the front and rear from the midpoint 26 to form a generally elongated elliptical configuration to conform with the configuration of the line of the user extending from the vaginal opening anteriorly and laterally to a point anterior of the urethra and provide a fluid tight engagement in the region of contact with the user.

Figure 10:
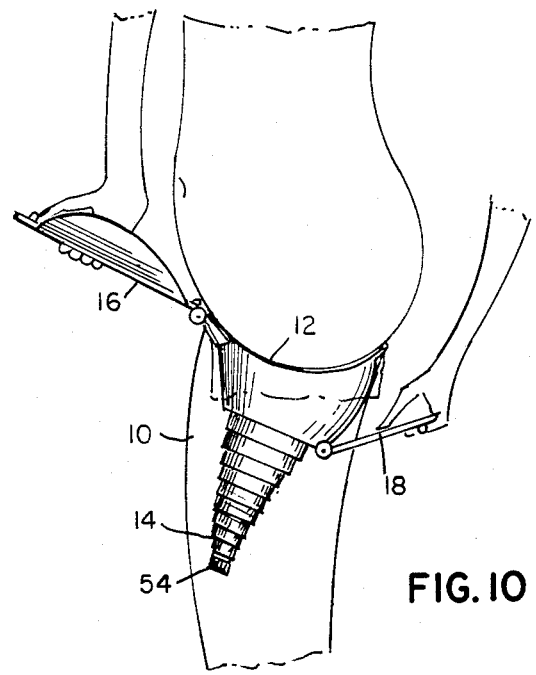
FIG. 10 is a view in perspective showing the use of the personal urinal device embodying the invention by a female in standing position.
Figure 11:
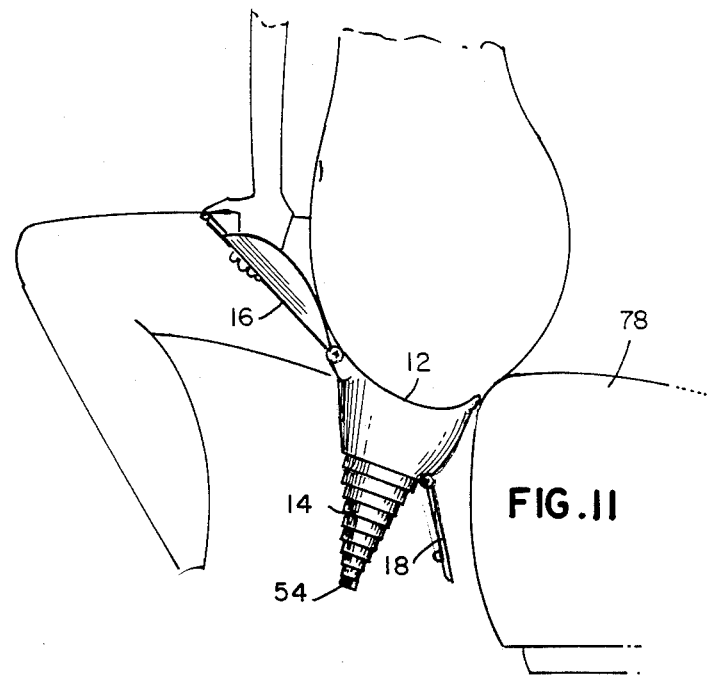

The cover 16 is attached to bowl 12 by a suitable hinge means 34 well known to those skilled in the art, and is provided with an edge 28 which corresponds in configuration to edge 26 of the bowl 12 so as to be in register therewith in the closed configuration. The cover 16 is also provided with a friction seal means about the periphery to provide a fluid tight seal. As illustrated, the seal comprises a groove 30 in the edge 24 of bowl 12 and a corresponding ridge 32 which is in sealing register with groove 30 in the closed position. The cover 16 preferably has an extension or lip 36 which extends outwardly beyond hinge 34. When the cover 16 is in a fully open position, lip 36 contacts housing 12 and prevents the cover 16 from swinging below about the horizontal plane of the upper edge of the bowl 12. While maintained in this open position, the cover serves as a handle which permits it to be gripped by the thumb and fingers of one hand of the user to aid in the manipulation of the urinal device 10 into and out of position and further permits it to be held firmly in position for use as best seen in FIGS. 10 and 11.

In a preferred embodiment, a removable absorbent material 38 is held on the inner side of cover 16 by resilient clip means 40. The absorbent material 38, which can be any commercially available tissue paper, can be employed by the user to remove any traces or urine on the user.

The lower flexible conductor member 14 has an upper annular flange member 42 which cooperates with the annular flange 44 of housing 12 to hold the lower member 14 in position when inserted through opening 22 of bowl 12. The lower conductor member 14 is preferable formed of a flexible water proof material which is constructed to open and close telescopically. Various plastic and water proof paper well known to those skilled in the art can be employed. The lower closure or cover member 18 is attached to the bowl 12 by hinge means 46 and is held in closed position by friction means comprising pin 48 and friction pin receptable 50. When in the closed position, lower cover 18 serves to hold lower conductor member 14 in folded position as best seen in FIG. 5.

When the urinal device 10 is to be employed as a temporary collector or receptacle for the discharged urine, the discharge opening 52 of the lower conductor member 14 is provided with a removable cap or seal 54. The removable cap 54 can be attached by suitable threads 56 or friction means (not shown) well known to those skilled in the art to provide a fluid light seal. In the collector mode of use the top cover 16 is closed after use to provide a fluid tight seal at the top. In the conductor mode, the lower member 14 is made sufficiently flexible so that during urination the user may direct the discharge opening to a suitable spot. In a preferred embodiment, the upper cover 16 is provided with a slight protrusion or extension 58 on the side opposite the hinge 34 which may be gripped by the finger to facilitate opening the upper cover. Similarly the lower cover 18 is provided with protrusion or extension 60. The lower cover 18 also serves an additional function as best seen in FIG. 10. As illustrated the lower cover 18 can be gripped by the thumb and finger of the users other hand and raised from its open position (shown by dotted lines) to the position shown and thereby provides additional means to hold the urinal device 10 firmly in position for use.

Figure 5:
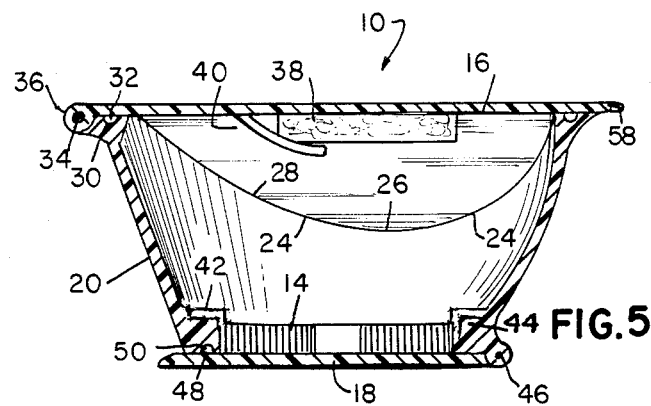
FIG. 5 is a side sectional view of the urinal device of FIG. 1 in closed position along the lines 5—5 of FIG. 3.
Figure 6:
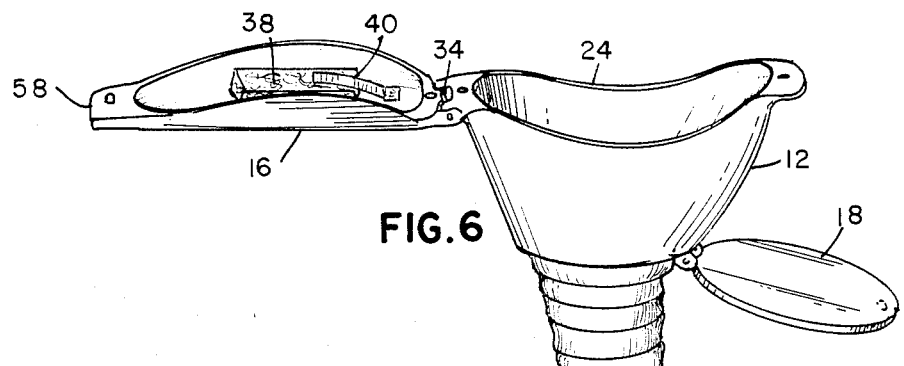
FIGS. 6 and 7 are perspective views illustrating alternate forms of the lower conductor member of the urinal device of FIG. 5.
Figure 7:
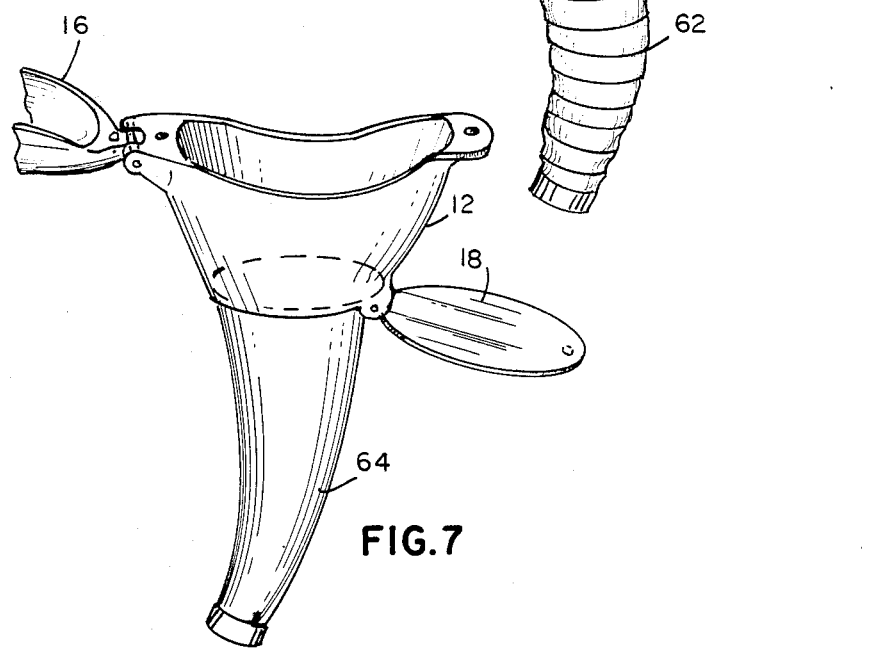

Referring now to FIGS. 6 and 7 of the drawings, there is illustrated alternate embodiments of the lower conductor member 14 of FIG. 5. The lower coductor member 62 is formed of corrigated material and folds accordian-like upon itself to a stored position within the bowl 12. Suitable corrugated material can be plastic, rubber or waterproof paper for example. As shown in FIG. 7, the lower conductor member 64 is formed of a relatively smooth material such as plastic, rubber or waterproof paper which is sufficiently flexible to easily foldable upon itself for storage within bowl 12.

Referring now to FIGS. 8 and 9 of the drawing, there is illustrated an alternate embodiment of the urinal device of the present invention. As illustrated in this embodiment, the housing 66 of bowl 12 terminates in an outward flange means 68 which receives the upper portion 70 of the lower conductor member 72, which is formed of a flexible or foldable material as described hereinbefore. The upper portion 70 is preferably thicker than the remainder of the lower conductor 72 and forms a ring or collar which is positioned about flange 68 and thereby held in place. It is to be understood that at least the upper portion 70 of conductor 72 may be formed of an elastic material to further secure the conductor 72 upon the flange 68 of bowl 12.

Referring now also to FIG. 9, the urinal device is shown in the closed mode. In this mode, the conductor 72 is folded and held within housing 66 by the lower cover 74. The peripheral edge of cover 74 is provided with a curved portion 76 which releasably cooperates with flange 68 to hold the cover in closed position. Various pliable plastic materials well known to those skilled in the art can be used to form the cover 74. In the preferred embodiment of the present invention, the bowl 12 is formed of a firmer or thicker material such as plastic, so as normally to maintain its configuration.

In typical use by a female, the upper and lower covers are opened and the lower conductor unfolded or extended into elongate position, and the seal cap over the discharge opening removed. The urinal device is then placed against the external vulva immediately prior to urination. The device is held firmly in position by the opened upper cover. When the situation and position permits the lower cover may be grasped for added firmness. During urination, the stream issuing from the discharge opening is directed to a suitable spot. Where circumstances require that the urine be temporarily stored, the seal cap is not removed. After urination where temporary storage is not required, the device is either washed and returned to the closed mode or immediately returned to the closed mode and stored for later washing. In an alternate embodiment of the urinal device of the present invention, wherein the lower conductor member is disposable and the upper bowl member is reusable, the lower conductor member is disengaged from the bowl member and suitable discarded, and the bowl member washed for reuse with a new lower conductor member engaged and/or stored within the bowl member.

Referring to FIG. 11, the urinal device is shown being used in a sitting position by a female user. The urinal device of the present invention enables a user to urinate under circumstances where no other facilities are available such as for example when riding in a motor vehicle and (as illustrated in FIG. 11) while in the sitting position on the seat 78 of an automobile (not shown). In this example the urinal device is used to temporarily store the discharged urine and has the sealing cap 54 secured in position. After urination is complete, the cover 16 is closed to prevent loss of urine from the urinal device which then serves to provide a temporary storage container.

It is to be understood that while the urinal device of the present invention has been described principally with respect to its use by females, there are circumstances where it is suitable for use by males. For example, such use by male would be when facilities are not available and the urinal device serves to receive and temporarily store discharge urine. In such use, the inner surface of the tapered housing 20 of upper bowl member 12 serves to define a sloping surface for supporting the penis on placement of said bowl in position for use.

While the invention has been described with respect to preferred embodiments, it will be apparent to those skilled in the art that changes and modifications may be made without departing from the scope of the invention herein involved in its broader aspects. Accordingly, it is intended that all matter contained in the above description, or shown in the accompanying drawing shall be interpreted as illustrated and not in limiting sense.

What is claimed is:

1. A personal urinal device for use by a female in a standing or sitting position comprising:
   a housing forming an elongated bowl member having an upper opening and a lower opening,
   said housing tapering downwardly from said upper opening to said lower opening,
   said upper opening including an edge having a generally elongated curvature sloping laterally and upwardly anteriorly and posteriorly to duplicate a line extending from the vaginal opening anteriorly and laterally generally coincident with the labia major to a point anterior of the urethra to thereby form a seal with the flesh of said female on placement of said bowl in position for use by said female,
   an elongated hollow conductor member adapted at one end to form a fluid tight seal with said lower opening of said bowl member and tapering to a discharge opening at the other end,
   said elongated hollow conductor member being sufficiently flexible to be compressed into flattened position within said bowl member prior to use,
   upper cover means attached to said bowl adjacent said upper opening and having at least the lower edge in configuration for fluid light seal when in register with said upper opening edge in closed position,
   said upper cover means opening forwardly of said bowl member to provide means for manual munipulation and holding of said urinal device, and
   lower cover mean attached to said bowl adjacent said lower opening for securing said opening prior to use,
   said lower cover means opening rearwardly of said bowl member to provide other means for manual munipulation and holding of said urinal device,
   said bowl member and said flexible elongated hollow conductor means cooperating to collect urine from said female and direct said urine to a suitable spot.

2. The personal urinal device of claim 1 further comprising a disposable moisture absorbent material removably attached to said upper cover means for absorbing residual traces of urine on said user.

3. The personal urinal device of claim 1 further comprising closure means associated with said discharge opening and adapted to releasably seal said discharge opening against the flow of urine.

4. The personal urinal device of claim 1 comprising means for frictionally holding said upper and lower cover means in closed position.

5. The personal urinal device of claim 4 wherein said upper and lower covers means are provided with tab protrusions for aiding in opening said upper and lower cover means.

6. A personal portable urinal device for collecting and temporary storage of urine from either a male or female in a standing or sitting position comprising:
   a housing forming an elongated bowl member having an upper opening and a lower opening,
   said housing tapering downwardly from said upper opening to said lower opening,
   said upper opening including an edge having a generally elongated curvature sloping laterally and upwardly anteriorly and posteriorly to duplicate a line extending from the vaginal opening anteriorly and laterally generally coincident with the labia major to a point anterior of the urethra to thereby form a seal with the flesh of said female on placement of said bowl in position for use by said female,
   said tapering housing further defining a sloping surface for supporting the penis in placement of said bowl in position for use by a male,
   an elongated hollow conductor member adapted at one end to form a fluid tight seal with said lower opening of said bowl member and tapering to a discharge opening at the other end,
   closure means associated with said discharge opening and adapted to releasably seal said discharge opening against the flow of urine,
   said elongated hollow conductor member being sufficiently flexible to be compressed into flattened position within said bowl member prior to use,
   upper cover means attached to said bowl adjacent said upper opening and having at least the lower edge in configuration for fluid tight seal when in register with said upper opening edge in closed position, said upper cover means opening forwardly of said bowl member to provide means for manual munipulation and holding of said urinal device, and lower cover mean attached to said bowl adjacent said lower opening for securing said opening prior to use, said lower cover means opening rearwardly of said bowl member to provide other means for manual munipulation and holding of said urinal device, said bowl member, cover means, elongated hollow conductor means and closure means cooperating to collect and store urine from said male or female.

* * * * *